United States Patent
Shirahase et al.

(10) Patent No.: US 6,262,108 B1
(45) Date of Patent: Jul. 17, 2001

(54) MEDICINAL USE OF CROMOGLYCIC ACID COMPOUNDS

(75) Inventors: Hiroaki Shirahase, Kyoto; Akihisa Yoshimi, Osaka; Shohei Nakamura; Mamoru Kanda, both of Kyoto; Fumio Fukata, Osaka, all of (JP)

(73) Assignee: Kyoto Pharmaceutical Industries, Ltd., Kyoto (JP)

(*) Notice: Subject to any disclaimer, the term of this patent is extended or adjusted under 35 U.S.C. 154(b) by 0 days.

(21) Appl. No.: 09/555,751
(22) PCT Filed: Nov. 30, 1998
(86) PCT No.: PCT/JP98/05393
  § 371 Date: Jul. 28, 2000
  § 102(e) Date: Jul. 28, 2000
(87) PCT Pub. No.: WO99/27926
  PCT Pub. Date: Jun. 10, 1999

(30) Foreign Application Priority Data

Dec. 3, 1997 (JP) .................................................. 9-332553

(51) Int. Cl.⁷ ........................... A61K 31/35; C07D 311/14
(52) U.S. Cl. ................................... 514/456; 549/402
(58) Field of Search .............................. 549/402; 514/456

(56) References Cited

U.S. PATENT DOCUMENTS

| 4,066,756 | 1/1978 | Orr et al. |
| 4,847,286 | 7/1989 | Tamaki et al. ............... 514/456 |

FOREIGN PATENT DOCUMENTS

| 0 916 338 | 5/1999 | (EP) . |
| 0 937 457 | 8/1999 | (EP) . |
| 62-81380 | 4/1987 | (JP) . |

OTHER PUBLICATIONS

Patent Abstracts of Japan, vol. 11, No. 282, p. 121 (Sep. 11, 1997) (Dialog Accession No. 02 164480) (JP 62–081380 A (Apr. 14, 1987)).

Iyakuhinyoran 5th ed., Osaka Hospital Pharmacist Association ed. (1992), and Medicina, 28(2), 257–261 (1991–92) [English abstract only].

Yoshimi et al., "Importance of Hydrolysis of Amino Acid Moiety in Water–Soluble Prodrugs of Disodium Cromoglycate for Increased Oral Bioavailability," *J. Pharmacobio-–Dyn.*, 15, 339–345 (1992).

Mori et al., "Pro–drugs for the Oral Delivery of Disodium Cromoglycate," *Chem. Pharm. Bull*, 36(1), 338–344 (1988).

*Primary Examiner*—Floyd D. Higel
*Assistant Examiner*—Andrea M D'Souza
(74) *Attorney, Agent, or Firm*—Leydig, Voit & Mayer, Ltd.

(57) ABSTRACT

The cromoglycic acid compound of the formula (I)

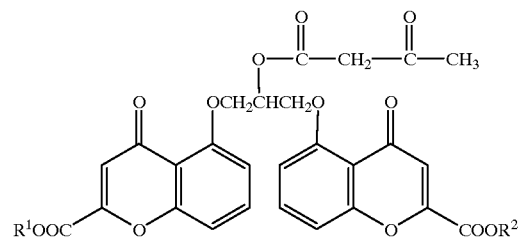

has an antirheumatic action, an antiinflammatory action and an immunomodulating action. This compound is effective for the inhibition of the symptoms of chronic rheumatoid arthritis and is associated with fewer side effects. Therefore, the antirheumatic agent of the present invention can be used beneficially for the treatment of rheumatoid arthritis. In addition, this compound has anti-type I and anti-type IV allergic activities. Therefore, the compound can be used beneficially mainly for the treatment of allergic dermatitis, in which a type IV allergic reaction is involved, such as contact dermatitis, in which a type IV allergic reaction is involved, atopic dermatitis, in which type I and type IV allergic reactions are involved and the like.

10 Claims, No Drawings

MEDICINAL USE OF CROMOGLYCIC ACID COMPOUNDS

This application is a 371 of PCT/JP 98/05393 dated Nov. 30, 1998.

TECHNICAL FIELD

The present invention relates to a pharmaceutical use of cromoglycic acid compound. More particularly, the present invention relates to a pharmaceutical use of a cromoglycic acid compound as an antirheumatic agent, a therapeutic agent for allergic dermatitis in which a type IV allergic reaction is involved, and a therapeutic agent for allergic dermatitis in which type I and type IV allergic reactions are involved, particularly, a therapeutic agent for contact dermatitis and a therapeutic agent for atopic dermatitis.

BACKGROUND ART

A typical rheumatic disease—chronic rheumatoid arthritis (hereinafter RA)—is a systemic disease of connective-tissue having a main symptom of polyarthritis chronica, and is one of the autoimmune diseases. The general disease type thereof is polyarthritis which is progressive and chronic. It includes various clinical types such as one showing spontaneous remission, one showing highly progressive destruction and absorption of joints (e.g., arthritis dissecans) and the like. Clinical symptoms thereof include arthritis, swelling of joint, pain, deformation, morning stiffness, rheumatoid nodule, angiitis and the like.

For internal therapy of RA at present, nonsteroidal antiinflammatory agents (e.g., aspirin, indometacin, diclofenac sodium, ibuprofen, loxoprofen sodium, piroxicam, ampiroxicam, naproxen, and the like), adrenocorticosteroidal agents (e.g., intraarticular injection and oral administration of prednisolone, and the like), immunomodulators (e.g., gold preparation, D-penicillamine, bucillamine, actarit and the like), immunosuppressive agents (e.g., methotrexate, mizoribine and the like), and the like are used. These medicaments, nevertherless, fail to provide sufficient therapeutic effects, but rather, cause various side effects. For example, nonsteroidal antiinflammatory agents may cause peptic ulcer, nephropathy, hepatopathy and the like, adrenocorticosteroidal agents may induce and exacerbate infectious diseases, diabetes, moon face, peptic ulcer, adrenocortical insufficiency, thrombophlebitis, osteoporosis and the like, immunomodulators may cause dermatopathy, nephropathy, stomatitis and the like, and immunosuppressive agents may cause hepatopathy, leukopenia, thrombocytopenia and the like, some of which constituting severe side effects.

Typical allergic dermatitis includes contact dermatitis, atopic dermatitis and the like.

The contact dermatitis is an inflammation of the skin, which is developed by the contact of a substance with the skin. The onset of the disease is seen when, for example, a certain substance, such as a plant (e.g., lacquer and the like), cosmetics, a detergent, clothes, commercially available external drug and the like, comes into contact with the skin and when the substance shows irritation property beyond the resistance threshold value of the individual or when the individual has been sensitized with the substance in contact. The onset of the contact dermatitis is caused by physicochemical properties of the substance, sensitization activity, contact frequency, disposition of the individual and the like. The disease type includes irritant dermatitis, phototoxic dermatitis, allergic dermatitis, photoallergic dermatitis, contact urticaria, systemic contact-type dermatitis and the like. The clinical symptoms of contact dermatitis include acute eczema accompanied by erythema, edema, papula, vesicle, erosion, itching and the like, and repetition thereof develops eczema accompanying lichenification and infiltration. The mechanism of the onset of these diseases is considered to be associated with a type IV allergic reaction (delayed type allergic reaction) caused by T cell. The type IV allergic reaction is induced by the reaction of sensitized T cell with antigen, which releases lymphokine from the sensitized T cell to cause cytotoxicity and the like, which in turn induces this allergic reaction.

The atopic dermatitis is developed by exogeneous disposition, namely, by various antigens, since the subject has an atopic disposition of hypersensitivity against a certain substance. The clinical symptoms include marked itching, skin hypertrophy, infiltration, lichenification and the like. The mechanism of the onset of this disease has been said to include a type I allergic reaction (immediate hypersensitivity) involving IgE, but it is inconclusive. In recent years, a type IV allergic reaction has been considered to be responsible for the onset of this disease, and in fact, the clinical symptoms of this disease are extremely similar to the symptoms of the above-mentioned contact dermatitis allegedly caused by a type IV allergic reaction.

Currently, anti-histamine agents and steroidal agents have been used as therapeutic agent for contact dermatitis, and these and a part of the so-called antiallergic agents have been mainly used for atopic dermatitis.

Examples of the anti-histamine agents include diphenhydramine hydrochloride, mequitazine, promethazine hydrochloride, chlorpheniramine maleate and the like, and they have been mainly used to reduce itchiness.

As the steroidal agents, prednisolone, hydrocortisone butyrate, dexamethasone valerate, betamethasone dipropionate, clobetasol propionate and the like have been used. While these show therapeutic effects, they also cause side effects of induced infection, secondary adrenal cortical insufficiency, diabetes, peptic ulcer, hirsutism, alopecia, pigmentation and the like, and they are remotely desirable therapeutic agents.

As the antiallergic agent, tranilast, ketotifen fumarate, oxatomide, azelastine hydrochloride and the like have been used. None of them shows satisfactory therapeutic effects and they are not used for contact dermatitis.

In general, conventional so-called antiallergic agents, such as tranilast, oxatomide, pemirolast potassium, repirinast, emedastine difumarate, epinastine hydrochloride and the like, are either ineffective or fail to show satisfactory therapeutic effects on contact dermatitis and atopic dermatitis that are considered to be mainly caused by a type IV allergic reaction. This is postulated to be due to the inhibitory action of these so-called antiallergic agents only on type I allergic reaction (immediate hypersensitivity), in which IgE is involved, and a failure to show a type IV allergic reaction-inhibitory action (Kobayashi, K. et al.:Japan. J. Pharmacol. 63, 73–81 (1993), Takemori Omori et al.: Folia Pharmacol. Jpn. 80, 261–270 (1982), Yanagihara, Y. et al.: Japan. J. Pharmacol. 51, 93–100 (1989), Kazuo Takahashi et al.: Folia Pharmacol. Jpn. 88, 245–254 (1986), Tadayuki-Saito et al.: Folia Pharmacol. Jpn. 89, 55–62 (1987), Kamei, C. et al.:Arzneim.-Forsch./Drug Res.41(II), 1150–1153).

Hence, a type IV allergic reaction-inhibitory action at the inflammation site is considered to be essential for the treatment of allergic dermatitis, particularly contact dermatitis and atopic dermatitis.

In the above-mentioned various situations, the development of an antirheumatic agent effective for the alleviation and inhibition of the symptoms of RA and associated with less side effects, and a highly safe and highly effective therapeutic agent for allergic dermatitis, in which a type IV allergic reaction is involved, particularly a therapeutic agent for contact dermatitis and a therapeutic agent for atopic dermatitis, have been demanded.

DISCLOSURE OF THE INVENTION

It is therefore an object of the present invention to provide an antirheumatic agent that is effective for the treatment of RA and that causes fewer side effects.

It is also an object of the present invention to provide a highly safe therapeutic agent effective for allergic dermatitis, such as contact dermatitis in which a type IV allergic reaction is involved, atopic dermatitis in which type I and type IV allergic reactions are involved, and the like.

The present inventors have conducted various studies in an attempt to achieve the above-mentioned objects and found that a cromoglycic acid compound of the formula (I) to be mentioned later [hereinafter to be also referred to as cromoglycic acid compound (I)] inhibits the symptoms of polyarthritis which is the main condition of RA. The present inventors have also found that the cromoglycic acid compound (I) is effective for the treatment of allergic dermatitis such as contact dermatitis wherein type IV allergic reaction is involved, atopic dermatitis wherein type I and type IV allergic reactions are involved, and the like, which resulted in the completion of the present invention.

Accordingly, the present invention provides the following.

1. A therapeutic agent for rheumatic diseases, which comprises a cromoglycic acid compound of the formula (I):

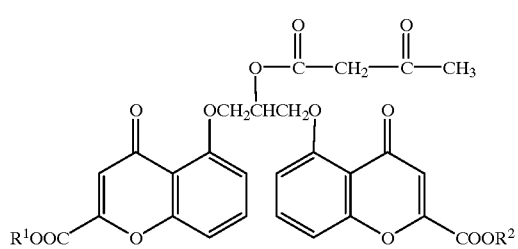

(I)

wherein $R^1$ and $R^2$ are each unsubstituted lower alkyl, as an active ingredient.

2. A therapeutic agent for allergic dermatitis in which a type IV allergic reaction is involved, which comprises the cromoglycic acid compound of the above formula (I) as an active ingredient.

3. A therapeutic agent for allergic dermatitis in which type I and type IV allergic reactions are involved, which comprises the cromoglycic acid compound of the above formula (I) as an active ingredient.

4. A therapeutic agent for contact dermatitis, which comprises the cromoglycic acid compound of the above formula (I) as an active ingredient.

5. A therapeutic agent for atopic dermatitis, which comprises the cromoglycic acid compound of the above formula (I) as an active ingredient.

6. A method for treating rheumatic diseases, comprising administering an effective amount of the cromoglycic acid compound of the above formula (I).

7. A method for treating allergic dermatitis in which a type IV allergic reaction is involved, comprising administering an effective amount of the cromoglycic acid compound of the above formula (I).

8. A method for treating allergic dermatitis in which type I and type IV allergic reactions are involved, comprising administering an effective amount of the cromoglycic acid compound of the above formula (I).

9. A method for treating contact dermatitis, comprising administering an effective amount of the cromoglycic acid compound of the above formula (I).

10. A method for treating atopic dermatitis, comprising administering an effective amount of the cromoglycic acid compound of the above formula (I).

11. Use of the cromoglycic acid compound of the above formula (I) for the production of a therapeutic agent for rheumatic diseases.

12. use of the cromoglycic acid compound of the above formula (I) for the production of a therapeutic agent for allergic dermatitis in which a type IV allergic reaction is involved.

13. Use of the cromoglycic acid compound of the above formula (I) for the production of a therapeutic agent for allergic dermatitis in which type I and type IV allergic reactions are involved.

14. Use of the cromoglycic acid compound of the above formula (I) for the production of a therapeutic agent for contact dermatitis.

15. Use of the cromoglycic acid compound of the above formula (I) for the production of a therapeutic agent for atopic dermatitis.

16. A pharmaceutical composition for the treatment of rheumatic diseases, which comprises an effective amount of the cromoglycic acid compound of the above formula (I) and a pharmaceutically acceptable carrier.

17. A pharmaceutical composition for the treatment of allergic dermatitis in which a type IV allergic reaction is involved, which comprises an effective amount of the cromoglycic acid compound of the above formula (I) and a pharmaceutically acceptable carrier.

18. A pharmaceutical composition for the treatment of allergic dermatitis in which type I and type IV allergic reactions are involved, which comprises an effective amount of the cromoglycic acid compound of the above formula (I) and a pharmaceutically acceptable carrier.

19. A pharmaceutical composition for the treatment of contact dermatitis, which comprises an effective amount of the cromoglycic acid compound of the above formula (I) and a pharmaceutically acceptable carrier.

20. A pharmaceutical composition for the treatment of atopic dermatitis, which comprises an effective amount of the cromoglycic acid compound of the above formula (I) and a pharmaceutically acceptable carrier.

21. A commercial package comprising the pharmaceutical composition of above 16 and a written matter associated therewith, the written matter stating that the pharmaceutical composition can or should be used for treating rheumatic diseases.

22. A commercial package comprising the pharmaceutical composition of above 17 and a written matter associated therewith, the written matter stating that the pharmaceutical composition can or should be used for treating allergic dermatitis in which a type IV allergic reaction is involved.

23. A commercial package comprising the pharmaceutical composition of above 18 and a written matter associated therewith, the written matter stating that the pharmaceutical composition can or should be used for treating allergic dermatitis in which type I and type IV used for treating allergic dermatitis in which type I and type IV allergic reactions are involved.

24. A commercial package comprising the pharmaceutical composition of above 19 and a written matter associated therewith, the written matter stating that the pharmaceutical composition can or should be used for treating contact dermatitis.

25. A commercial package comprising the pharmaceutical composition of above 20 and a written matter associated therewith, the written matter stating that the pharmaceutical composition can or should be used for treating atopic dermatitis.

DETAILED DESCRIPTION OF THE INVENTION

Examples of the unsubstituted lower alkyl at $R^1$ and $R^2$ in the formula (I) are preferably straight-chained or branched alkyl having 1 to 4 carbon atoms, such as methyl, ethyl, propyl, isopropyl, butyl, tert-butyl and the like.

The cromoglycic acid compound (I) of the present invention is a known compound and can be produced by a method known per se. For example, the cromoglycic acid compound (I) can be produced by the method disclosed in JP-A-62-81380, that is, by reacting a compound (II) of the formula (II)

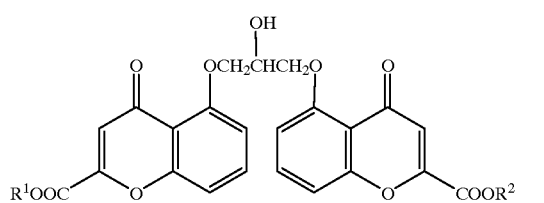

(II)

wherein $R^1$ and $R^2$ are as defined above, and a compound (III) of the formula (III)

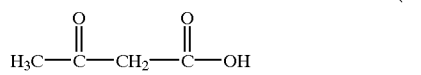

(III)

or a compound (IV) of the formula (IV)

(IV)

In this reaction, the compound (III) is subjected to the reaction as a free carboxylic acid or a reactive derivative thereof.

The cromoglycic acid compound (I) thus produced can be formulated into a dosage form suitable for parenteral administration (percutaneous administration, intravenous injection, intramuscular injection, subcutaneous injection, intraarticular injection, intratendonic injection etc.) or oral administration by a known method, such as capsule, tablet, fine granules, granules, dry syrup, injection, suspension, emulsion, ointment, lotion, cream, liquid, eye drop, aerosol and the like, and can be used as an antirheumatic agent and a therapeutic agent for allergic dermatitis, such as a therapeutic agent for contact dermatitis, a therapeutic agent for atopic dermatitis and the like.

The antirheumatic agent and the therapeutic agent for allergic dermatitis may contain, where necessary, conventional additives such as an excipient (e.g., starch, lactose, sugar, calcium carbonate, calcium phosphate etc.), a binder (e.g., starch, gum arabic, carboxymethylcellulose, hydroxypropylcellulose, crystalline cellulose, polyvinylpyrrolidone etc.), a lubricant (e.g., magnesium stearate, talc etc.), a disintegrant (e.g., calcium carboxymethylcellulose, talc etc.), a suspending agent (e.g., methylcellulose etc.), a stabilizer, an emulsifier, a solubilizer, a corrective, a buffer and the like.

The antirheumatic agent obtained according to the present invention can be advantageously used for the treatment of rheumatism because it has an antirheumatic action, an antiinflammatory action and an immunomodulating action, and is effective for inhibition of the symptoms of RA.

The therapeutic agent for allergic dermatitis, which is obtained according to the present invention, has an anti-type I allergic activity and an anti-type IV allergic activity. Therefore, it can be advantageously used as a therapeutic agent for allergic dermatitis, particularly as a therapeutic agent for contact dermatitis and atopic dermatitis.

When this therapeutic agent is administered, the daily dose is preferably administered in 1 to 4 times. While the dose varies depending on the symptom, age, body weight and the like of patients, when converted to the amount of cromoglycic acid compound (I) which is an active ingredient, the daily dose for an adult will be 5–1500 mg.

The present invention is explained in more detail in the following by referring to Examples and Experimental Examples. The present invention is not limited to these.

EXAMPLE 1

Synthesis of Diethyl Acetoacetylcromoglycate

Methylene chloride (700 ml) was added to diethyl cromoglycate (25 g, 47.7 mmol) and 4-dimethylaminopyridine (2.9 g, 23.8 mmol, 0.5-fold mole), and, while stirring to give a suspension, diketene (8.0 g, 95 mmol) was added 4 times at 5° C. every 30 min (total 32 g, 380 mmol, 8-fold moles). The mixture was stirred at 5–10° C. for 2.5 hr. The reaction mixture was washed with 5% aqueous citric acid solution (500 ml) and saturated brine (500 ml), and dried over anhydrous sodium sulfate. The drying agent was filtered off and methylene chloride was evaporated under reduced pressure. The obtained residue was dissolved in 99.5% ethanol (160 ml) while hot (65–70° C.), and concentrated under reduced pressure until crystals started to precipitate, which was followed by standing at 5° C. for 15 hr. The precipitated crystals were collected by filtration, washed successively with cold ethanol and isopropyl ether, and dried to give crystals of diethyl acetoacetylcromoglycate at a yield of 36 g.

IR(KBr, cm$^{-1}$): 1730, 1650. NMR (CDCl$_3$, δ ppm): 1.41 (6H, t, J=7Hz, —CH$_2$CH$_3$), 2.28(3H, s, —COCH$_3$), 3.57 (2H, s, —COCH$_2$CO—), 4.41(4H, q, J=7Hz, —CH$_2$CH$_3$), 4.3–4.9(4H, m,

), 5.4–6.0(1H, m,

6.84(2H, s, chromone 3-position —H), 6.92–7.28(4H, m, chromone 6-position, 8-position —H), 7.57(2H, t, J=9Hz, chromone 7-position —H).

EXPERIMENTAL EXAMPLE 1
Acute Toxicity Test

The cromoglycic acid compound prepared in the above Example 1 was orally administered to male ICR mice (3 per group) in the form of a suspension. The results are shown in the following Table 1.

TABLE 1

|  | $LD_{50}$ (mg/kg) |
| --- | --- |
| Compound produced in Example 1 | >1000 |

FORMULATION EXAMPLE 1

The tablets having the following recipe are produced by a conventional method.
Compound of Example 1 5 mg
Polyvinylpyrrolidone 20 mg
Starch 75 mg
Magnesium stearate 2 mg

EXPERIMENTAL EXAMPLE 2
Inhibition of Collagen-induced Arthritis by Diethyl Acetoacetylcromoglycate in Mice According to the method of Courtenay et al. (Courtenay, J. S. et al.: Immunization against heterologous type II collagen induces arthritis in mice. Nature, 283:666, 1980), male DBA/1J mice (CHARLES RIVER JAPAN INC.) were sensitized with bovine type II collagen to induce collagen-induced arthritis (rheumatoid arthritis). After the onset of arthritis, diethyl acetoacetylcromoglycate was orally administered and its inhibitory effect was examined. The method is detailed in the following.

Male DBA/1J mice (8-week-old) were pre-bred for one week and divided into the following 3 groups based on body weight (8–10 per group).
(1) Normal group
(2) Control group
(3) Treated group Bovine type II collagen (2 mg) was dissolved in 0.01M acetic acid (1 ml) and suspended in an equivalent amount of Freund's complete adjuvant, and 0.1 ml thereof was intradermally injected to the control group and treated group at 9 weeks of age at the base of the tail, followed by the second injection three weeks later at 12 weeks of age.

Starting from day 31 after the initial injection of collagen till the end of the treatment, the mice of each group were scored (arthritis score) twice a week for the levels of redness, swelling and stiffness of four limbs by a blind test method. The scores were taken according to a method similar to the method of Bjork et al. (Bjork, J. and Kleinau, S.: Paradoxical effects of LS-2616 (Linomide) treatment in the type II collagen arthritis model in mice, Agents and Actions, 27:319–321, 1989.), wherein normal was rated 0 point, inflammation on one digit was 1 point, inflammation on two or more digits and normal metacarpal region and metatarsal region of the limbs, or inflammation on one digit and metacarpal region and metatarsal region of the limbs was 2 points, and inflammation on digits and metacarpal region and metatarsal region of the limbs was 3 points, each mouse scoring 0 to 12 points in total.

At day 38 from the initial injection of collagen, the onset of arthritis was found in the control group and treated group. The arthritis score did not vary between the groups.

The treatment was continued for 6 weeks from day 41 from the initial injection of collagen. To be specific, diethyl acetoacetylcromoglycate was dissolved in 0.5% methylcellulose solution and forcefully administered orally to the mice of the treated group at a dose of 100 mg/kg/day, converted to diethyl acetoacetylcromoglycate, once a day for 6 weeks. A 0.5% methylcellulose solution (10 ml/kg/day) was given to the control group in the same manner.

The arthritis scores of each group at 3 days before the initiation of treatment and day 38 after the initiation of treatment are shown in Table 2. Comparative testing by U-test with control group showed a significant improvement in the arthritis scores of the treated group at day 38 after the start of the treatment.

TABLE 2

| | Arthritis score | |
| --- | --- | --- |
| | day 38 after initial injection of collagen (3 days before treatment) | day 79 after initial injection of collagen (day 38 after starting treatment) |
| normal group | 0.00 ± 0.00 | 0.00 ± 0.00** |
| control group | 1.70 ± 0.53 | 10.70 ± 0.49 |
| treated group | 1.80 ± 0.61 | 6.36 ± 1.30** |

Each value shows mean ± standard error (n = 8–10).
**:p < 0.01 (U-test relative to control group)

At day 42 after the initiation of treatment, blood was taken from carotid artery and the mice were exsanguinated to death under ether anesthesia. The anti-bovine type II collagen antibody titer in blood was determined by the ELISA method according to the method of Stuart et al. (Stuart, J. M. et al.: Nature and specificity of the immune response to collagen in type II collagen-induced arthritis in mice, J. Clin. Invest., 69:673–683, 1982). The results are shown in Table 3. Comparative testing by ANOVA method with the control group revealed a significant decrease in anti-bovine type II collagen antibody titer in blood in the treated group.

TABLE 3

| | Anti-bovine type II collagen antibody titer in blood |
| --- | --- |
| | day 83 after initial injection of collagen (day 42 after starting treatment) |
| normal group | 0.000 ± 0.000 ** |
| control group | 0.301 ± 0.005 |
| treated group | 0.203 ± 0.010 ** |

Each value shows mean ± standard error (n = 8–10).
** :p < 0.01 (ANOVA method test relative to control group)

In addition, the whole body was X-ray photographed and destruction state of the bone of feet and digits of the four limbs was scored (X-ray score) by a blind test according to the criteria of Gliman et al. (Gliman S. C. et al.: Immunological abnormalities in rats with adjuvant-induced ar thritis, II. Effect of antiarthritic therapy on immune function in relation to disease development, Int. J. Immunopharmacol., 9:9–16, 1987), wherein normal was rated 0 point, destruction in one joint was 1 point, destruction in two or more joints, though not all joints, was 2 points, and destruction in all joints was 3 points, each mouse scoring 0 to 12 points in total. The results are shown in Table 4. Comparative testing by U-test with the control group revealed a signifiicant improvement in X-ray so re in the treated group.

TABLE 4

X-ray score day 83 after initial injection of collagen
(day 42 after starting treatment)

| normal group | 0.00 ± 0.00** |
| control group | 10.20 ± 0.40 |
| treated group | 5.80 ± 1.10** |

Each value shows mean ± standard error (n = 8–10).
**:p < 0.01 (U-test relative to control group)

The collagen-induced arthritis in the mice used in this experiment is one of the test models of autoimmune arthritis most similar to human RA.

The administration of diethyl acetoacetylcromoglycate resulted in the inhibition of the symptoms of collagen-induced arthritis (rheumatoid arthritis) and inhibition of bone destruction of feet and digits of the four limbs as evidenced in X-ray photographs. Therefrom it follows that the compound has an anti-inflammatory action and an anti-rheumatic action. Moreover, the inhibition of an increase in the anti-bovine collagen antibody titer in blood indicated some immunomodulating action of this compound.

EXPERIMENTAL EXAMPLE 3

Type IV Allergic Dermatitis-inhibitory Action by Diethyl Acetoacetylcromoglycate Male 6-week-old ICR mice (Clea Japan, Inc.) were divided into two groups of control group and administration group containing 8–9 mice each. A 0.5% methylcellulose solution (10 ml/kg) was forcefully administered orally to the control group and diethyl acetoacetylcromoglycate (100 mg/kg) was forcefully administered orally to the administration group twice a day for 14 days for each group. After the initial administration at day 8 of the administration, pentobarbital sodium (55 mg/kg) was intraperitoneally administered to each mouse and the abdomen was shaved. 5% Picryl chloride (50 μl) dissolved in acetone-olive oil (mixing ratio, 1:4) was applied to the shaved portion (diameter about 2 cm). After the initial administration at day 5 after the application (day 12 of administration), all mice were anesthetized with ether and the thickness of both auricles was measured with a dial thickness gauge (Mitutoyo Co.). 0.5% Picryl chloride (10 μl) dissolved in acetone-olive oil (mixing ratio, 1:4) was applied to the both sides of the right auricle and acetone-olive oil (10 μl, mixing ratio, 1:4) was applied to the both sides of the left auricle. After 48 hours from this antigen challenge, the thickness of both auricles was measured with a dial thickness gauge under ether anesthesia.

The difference between the thickness of the auricle applied with the solvent and the thickness of the auricle applied with the antigen was measured for each mouse. The results are shown in Table 5. Comparative testing with the control group by t-test revealed a significant inhibitory action on the swelling of the auricle.

TABLE 5

Increase in thickness of the auricle at 48 hr after applying 0.5% picryl chloride solution (unit:mm)

| | control group | administration group |
| --- | --- | --- |
| Increase in thickness of auricle after application of antigen | 0.045 ± 0.003 | 0.031 ± 0.003 ** |

Each value shows mean ± standard error (n = 8–9).
** :p < 0.01 (t-test relative to control group)

EXPERIMENTAL EXAMPLE 4

Test of Type I and Type IV Allergic Dermatitis Inhibitory Action of Diethyl Acetoacetylcromoglycate According to the method of Nagai et al., (Naoki Inagaki and Hiroichi Nagai, The 8th Spring Meeting of Japanese Society of Allergology, 1996), the inhibitory action of diethyl acetoacetylcromoglycate on type I and type IV allergic dermatitis was examined.

According to this method, a type I allergic reaction is induced in addition to a type IV allergic reaction due to repeat contact sensitization with antigen. Therefore, the method has been proposed as a superior animal model of atopic dermatitis in human. The method is described in detail in the following.

Male 6-week-old BALB/c mice (Japan SLC, Inc.) were divided into two groups of control group and administration group including 10 mice each. A 0.5% methylcellulose solution (10 ml/kg) was forcefully administered orally to the control group and diethyl acetoacetylcromoglycate (100 mg/kg) was forcefully administered orally to the administration group twice a day for 36 days for each group. The thickness of both auricles of each mouse was measured with a dial thickness gauge (Mitutoyo Co.) under ether anesthesia before initial administration on day 1 after administration. After the initial administration on day 8 of the administration, the thickness of both auricles of each mouse was measured with a dial thickness gauge under ether anesthesia. 0.2% Dinitrofluorobenzene (DNFB) dissolved in acetone-olive oil (mixing ratio 3:1) was applied by 25 μl to the left and right auricles. After 24 hours from the application, the thickness of both auricles of each mouse was measured under ether anesthesia with a dial thickness gauge. Thereafter, similar manipulation was repeated 4 times at a week interval. At the 5th application, the thickness of both auricles was also measured at 1 and 4 hours after the application.

Changes in the thickness of both auricles of each mouse were calculated from the measurement values of the thickness of the both auricles before the initial application. The average of changes in the thickness of the left and right auricles of each mouse was taken as the variation of the mouse. The results are shown in Table 6.

TABLE 6

Increase in thickness of auricle by repeat application of 0.2% DNFB solution (unit:mm)

| | Control group | Administration group (100 mg/kg) |
|---|---|---|
| before 1st application | 0.008 ± 0.003 | 0.008 ± 0.002 |
| 24 hr after 1st application | 0.011 ± 0.002 | 0.012 ± 0.002 |
| before 2nd application | 0.033 ± 0.003 | 0.029 ± 0.003 |
| 24 hr after 2nd application | 0.048 ± 0.004 | 0.037 ± 0.003 * |
| before 3rd application | 0.042 ± 0.005 | 0.035 ± 0.003 |
| 24 hr after 3rd application | 0.092 ± 0.009 | 0.061 ± 0.005 ** |
| before 4th application | 0.049 ± 0.004 | 0.040 ± 0.005 |
| 24 hr after 4th application | 0.141 ± 0.012 | 0.095 ± 0.009 ** |
| before 5th application | 0.059 ± 0.006 | 0.048 ± 0.005 |
| 1 hr after 5th application | 0.098 ± 0.012 | 0.058 ± 0.007 * |
| 4 hr after 5th application | 0.063 ± 0.007 | 0.056 ± 0.007 |
| 24 hr after 5th application | 0.182 ± 0.015 | 0.122 ± 0.010 ** |

Each value shows mean ± standard error (n = 8–9).
* $p < 0.05$,
** $p < 0.01$ (t-test relative to control group)

The thickness of auricle before the initial application did not differ between the both groups. The repeat application of a 0.2% DNFB solution resulted in an increase in the thickness of auricle with time. Comparative testing with the control group by the t-test revealed a significant inhibitory action on the swelling of the auricle after the second application in the administration group.

At one hour after the fifth application, a transient noticeable increase in the thickness of the auricle was observed in the control group, which was a type I allergic reaction, but a significant inhibitory action on the swelling of the auricle was found in the administration group.

INDUSTRIAL APPLICABILITY

The cromoglycic acid compound (I) to be used in the present invention has an antirheumatic action, an antiinflammatory action and an immunomodulating action. This compound is effective for the inhibition of the symptoms of chronic rheumatoid arthritis and associated with fewer side effects as compared to conventional antirheumatic agents. Hence, the antirheumatic agent of the present invention containing this compound as an active ingredient is highly safer than the conventional antirheumatic agents and can be used beneficially for the treatment of rheumatoid arthritis.

The cromoglycic acid compound (I) to be used in the present invention has anti-type I and anti-type IV allergic activities, and is mainly effective for contact dermatitis induced by a type IV allergic reaction and atopic dermatitis induced by type I and type IV allergic reactions, on which conventional antiallergic agents have failed to produce sufficient effects. Therefore, a therapeutic agent for allergic dermatitis of the present invention containing this compound as an active ingredient can be used beneficially as a therapeutic agent effective for allergic dermatitis in general, in which a type IV allergic reaction is involved, particularly allergic dermatitis such as dermatitis caused by the contact of antigenic substance with the skin, and the like.

This application is based on application No. 332553/1997 filed in Japan, the contents of which are incorporated hereinto by reference.

What is claimed is:

1. A method for treating rheumatic diseases, comprising administering an effective amount of a cromoglycic acid compound of the formula (I)

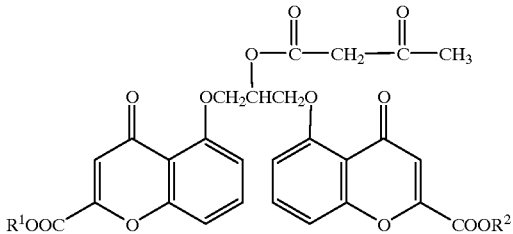

wherein $R^1$ and $R^2$ are each unsubstituted lower alkyl.

2. A method for treating allergic dermatitis in which a type IV allergic reaction is involved, comprising administering an effective amount of a cromoglycic acid compound of the formula (I)

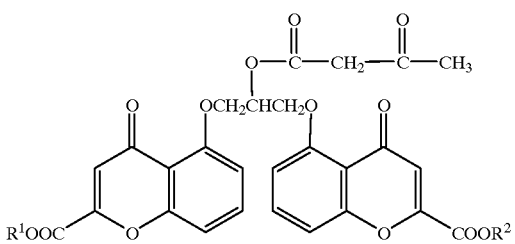

wherein $R^1$ and $R^2$ are each unsubstituted lower alkyl.

3. The method of claim 2, wherein said allergic dermatitis involves type I and type IV allergic reactions, and wherein said method comprises administering an effective amount of a cromoglyic acid compound of the formula (I)

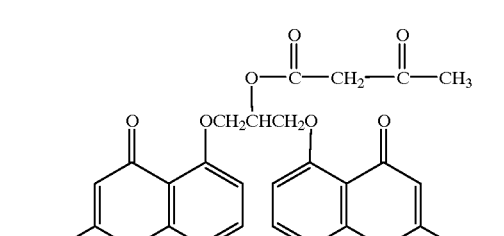

wherein $R^1$ and $R^2$ are each unsubstituted lower alkyl.

4. A method for treating contact dermatitis, comprising administering an effective amount of a cromoglycic acid compound of the formula (I)

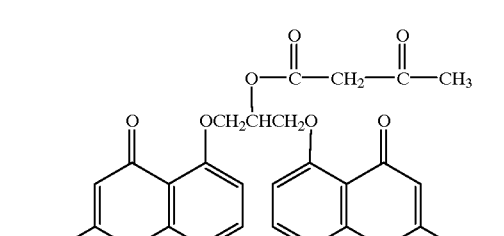

wherein $R^1$ and $R^2$ are each unsubstituted lower alkyl.

5. A method for treating atopic dermatitis in which a type IV allergic reaction is involved, comprising administering an effective amount of a cromoglyic acid compound of the formula (I)

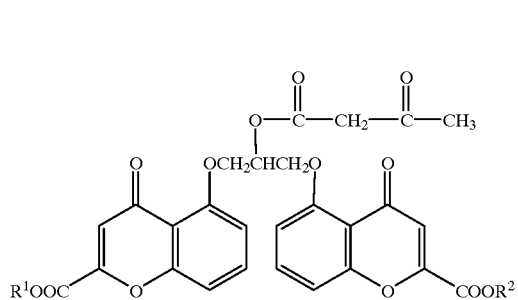

(I)

wherein $R^1$ and $R^2$ are each unsubstituted lower alkyl.

6. A method of treating rheumatic diseases, comprising administering an effective amount of a cromoglycic acid compound of the formula (I)

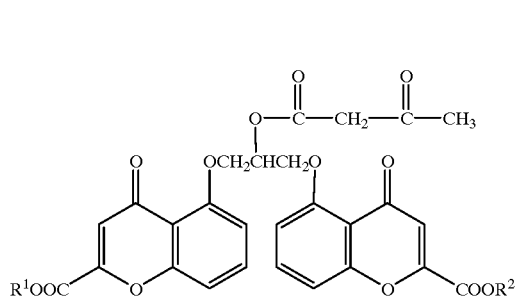

(I)

wherein $R^1$ and $R^2$ are each unsubstituted lower alkyl, and a pharmaceutically acceptable carrier.

7. A method of treating allergic dermatitis in which a type IV allergic reaction is involved, comprising administering an effective amount of a cromoglycic acid compound of the formula (I)

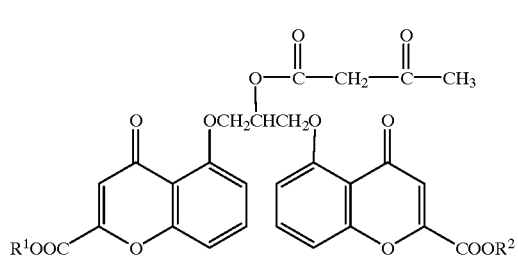

(I)

wherein $R^1$ and $R^2$ are each unsubstituted lower alkyl, and a pharmaceutically acceptable carrier.

8. A method of treating allergic dermatitis in which type I and type IV allergic reactions are involved, comprising administering an effective amount of a cromoglycic acid compound of the formula (I)

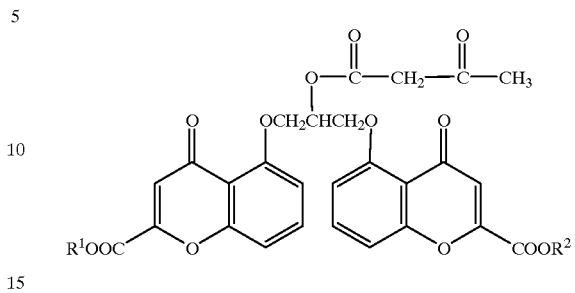

(I)

wherein $R^1$ and $R^2$ are each unsubstituted lower alkyl, and a pharmaceutically acceptable carrier.

9. A method of treating contact dermatitis, comprising administering an effective amount of a cromoglycic acid compound of the formula (I)

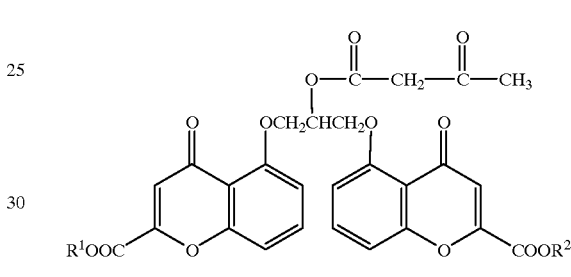

(I)

wherein $R^1$ and $R^2$ are each unsubstituted lower alkyl, and a pharmaceutically acceptable carrier.

10. A method of treating atopic dermatitis in which a type IV allergic reaction is involved, comprising administering an effective amount of a cromoglycic acid compound of the formula (I)

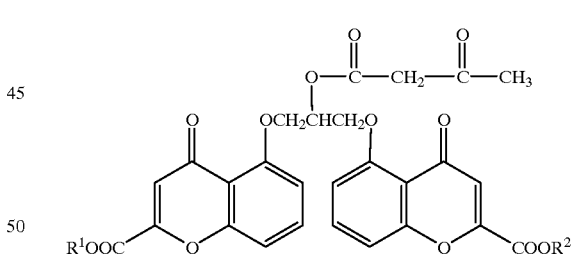

(I)

wherein $R^1$ and $R^2$ are each unsubstituted lower alkyl, and a pharmaceutically acceptable carrier.

* * * * *

UNITED STATES PATENT AND TRADEMARK OFFICE
CERTIFICATE OF CORRECTION

PATENT NO. : 6,262,108 B1
DATED : July 17, 2001
INVENTOR(S) : Shirahase et al.

Page 1 of 1

It is certified that error appears in the above-identified patent and that said Letters Patent is hereby corrected as shown below:

<u>Column 13, claim 5,</u>
Lines 1-2, "in which a type IV allergic reaction is involved" should be deleted.

<u>Column 14, claim 10,</u>
Lines 36-37, "in which a type IV allergic reaction is involved" should be deleted.

Signed and Sealed this

Sixteenth Day of April, 2002

*Attest:*

JAMES E. ROGAN
*Attesting Officer*          *Director of the United States Patent and Trademark Office*